US007223604B1

(12) United States Patent
Liu et al.

(10) Patent No.: US 7,223,604 B1
(45) Date of Patent: May 29, 2007

(54) METHODS AND KITS FOR THE DETECTION OF ERYTHROCYTES

(75) Inventors: Shimin Liu, Albuquerque, NM (US); Ke J. Liu, Albuquerque, NM (US)

(73) Assignee: Science & Technology Corporation @ UNM, Albuquerque, NM (US)

( * ) Notice: Subject to any disclaimer, the term of this patent is extended or adjusted under 35 U.S.C. 154(b) by 186 days.

(21) Appl. No.: 10/673,538

(22) Filed: Sep. 29, 2003

Related U.S. Application Data

(60) Provisional application No. 60/414,017, filed on Sep. 27, 2002.

(51) Int. Cl.
*G01N 33/72* (2006.01)
(52) U.S. Cl. ............................ 436/66; 436/63; 436/164; 436/172; 422/82.05; 422/82.08
(58) Field of Classification Search .................. 436/63, 436/66, 164, 172; 422/61, 82.05, 82.08
See application file for complete search history.

(56) References Cited

U.S. PATENT DOCUMENTS

| | | | | |
|---|---|---|---|---|
| 4,378,971 | A * | 4/1983 | Schwartz | ...................... 436/66 |
| 5,563,071 | A | 10/1996 | Augurt | |
| 5,665,308 | A | 9/1997 | Watanabe | |
| 5,702,913 | A | 12/1997 | Guadagno | |
| 5,840,584 | A | 11/1998 | Waldenburg | |
| 5,922,544 | A | 7/1999 | Miyai et al. | |
| 5,929,031 | A * | 7/1999 | Kerwin et al. | ................. 514/12 |
| 6,207,113 | B1 | 3/2001 | Kagaya | |
| 2004/0171016 | A1* | 9/2004 | Tomita et al. | .................. 435/6 |

OTHER PUBLICATIONS

Liu et al. Journal of Cerebral Blood Flow & Metabolism, vol. 22(10), Oct. 2002, pp. 1222-1230.*
Ahlquist et al. "Accuracy of fecal occult blood screening for colorectal neoplasia. A prospective study using Hemoccult and HemoQuant tests" *JAMA* 1993;269(10):1262-67.
Ahlquist, "Approach to the patient with occult gastrointestinal bleeding:" In: Yamada ed. *Textbook of gastroenterology*, 2(1) Philadelphia J.B. Lippincott, 1995;699-717.
Ahlquist et al. "Patterns of occult bleeding in asymptomatic colorectal cancer." *Cancer* 1989;63:1826-30.
Allison et al. "A comparison of fecal occult-blood tests for colorectal-cancer screening." *N Engl J Med* 1996;334(3):155-9.
Ames et al. "Cerebral ischemia. II. The no-reflow phenomenon" *Am J Pathol* 1968:52:437-53.
Bederson et al. "Evaluation of 2, 3, 5-Triphenyltetrazolium Chloride as a Stain for Detection and Quantification of Experimental Cerebral Infraction in Rats" *Stroke* 1986;17(6):1304-8.
Byers et al., American Cancer Society guidelines for screening and surveillance for early detection of colorectal polyps and cancer. Update 1997. *CA Cancer J Clin* 1997;47(3):154-60.
Clancy et al. "Reduction of background autofluorescence in brain sections following immersion in sodium borohydride." *J Neurosci Methods* 1998;83:97-102.

Czurkó et al. "'Collapsed' (argyophilic, dark) neurons in rat model of transient focal cerebral ischemia" *Neurosci Ltt.* 1993:162:71-4.
Eisner et al. "Diagnostic yield of a positive fecal occult blood test found on digital rectal examination. Does the finger count?" *Arch Intern Med* 1991;151:2180-4.
Ferrucci, Joseph T., "Colonoscopy and barium enema: radiologist's response." *Gastroenterology* 1997;112(1):294-7.
Fleisher et al. "Accuracy of fecal occult blood test interpretation." *Ann Intern Med* 1991;114(10):875-6.
Gouterman, Martin, "Optical Spectra and Electronic Structure of Porphyrins and Related Rings," *The Porphyrins*, vol. III , New York:Academic Press 1978; title page, pp. 1-165.
"Hemoccult fecal blood test" datasheet [online]. Beckman Coulter, Inc. Fullerton, CA, [retrieved on Sep. 22, 2005]. Retrieved from the Internet:<URL: www.beckman.com/products/RapidTestKits/hemoccult.asp>; 3 pgs.
Hermann et al. "Relationship between metabolic dysfunctions, gene responses and delayed cell death after mild focal cerebral ischemia in mice," *Neuroscience* 2001;104/(4);947-955.
Kalimo et al. "Structural aspects of ischemic brain damage" Acta Neurochir Suppl (Wien) 1986:36,129-32.
Lang et al. "Fecal occult blood screening for colorectal cancer. Is mortality reduced by chance selection for screening colonoscopy?" *JAMA* 1994;271(13):1011-3.
Lide, ed., *CRC Handbook of Chemistry and Physics*, Boca Raton, Florida 1999; cover page, title page and table of contents, 8-21-8-31.
Liu et al. "Visualization of the early "no-reflow phenomenon" in rats subjected to focal cerebral ischemia and reperfusion" *Society for Neuroscience Abstracts* 2001;27(1):1157. Abstract Only.
Longa et al. "Reversible Middle Cerebral Artery Occlusion Without Craniectomy in Rats" *Stroke* 1989;20(1):84-91.
Mandel et al. "Colorectal Cancer Mortality: Effectiveness of Biennial Screening for Fecal Occult Blood" *J of the National Cancer Institute* 1999;91(5):434-7.
Mandel et al. "Reducing mortality from colorectal cancer by screening for fecal occult blood" *N Engl J Med* 1993;328(19):1365-71.
Onizuka et al. "Early cytopathic features in rat ischemia model and reconstruction by neural graft." *Exp Neurol* 1996;137(2), 324-32.
"Package Insert EZ Detect Product" datasheet [online]. Test Medical Symptoms @ Home, Inc., Maria Stein, OH [retrieved on Sep. 22, 2005]. Retrieved from the Internet:<URL: www.testsymptomsathome.com/BII01_package_insert.asp>; 7 pgs.
Petito et al. "DNA fragmentation follows delayed neuronal death in CA1 neurons exposed to transient global ischemia in the rat." *J Cereb Blood Flow Metab* 1997;17(9):967-976.

(Continued)

*Primary Examiner*—Maureen M. Wallenhorst
(74) *Attorney, Agent, or Firm*—Mueting, Raasch and Gebhardt, P.A.

(57) ABSTRACT

Methods and kits useful in the detection of occult blood in biological samples and specimens, for example to screen for colorectal cancer or detect blood in samples ex vivo, e.g., at a crime scene. Also provided are methods useful in diagnosing whether a subject is predisposed to, or suffers from, an occult-blood related disorder; and methods for direct micro-mapping of the distribution of occluded vessels associated with cerebral vascular injury.

21 Claims, 8 Drawing Sheets

OTHER PUBLICATIONS

Radovsky et al. "Ischemic neurons in rat brains after 6, 8, or 10 minutes of transient hypoxic ischemia." *Toxicol Pathol* 1997;25(5):500-5.

Rex et al. "Relative sensitivity of colonoscopy and barium enema for detection of colorectal cancer in clinical practice." *Gastroenterology* 1997;112(1):17-23.

Rockey et al. "Relative frequency of upper gastrointestinal and colonic lesions in patients with positive fecal occult-blood tests." *N Engl J Med* 1998;339(3):153-9.

Rockey et al. "Detection of Upper Gastrointestinal Blood with Fecal Occult Blood Tests" *Am. J. Gastroenterol* 1999;94(2):344-50.

Schwartz et al. "The "HemoQuant" test: a specific and quantitative determination of heme (hemoglobin) in feces and other materials." *Clin Chem* 1983;29(12):2061-7.

Stroehlein et al., "Hemoccult detection of fecal occult blood quantitated by radioassay." *Am J Dig Dis* 1976;21:841-44.

Tanaka et al. "Induction of glyceraldehyde-3-phosphate dehyrogenase (GAPDH) expression in rat brain after focal ischemia/reperfusion" *Journal of Cerebral Blood Flow and Metabolism* 2002;22(3):280-8.

United States Preventive Services Task Force. Guide to Clinical Preventive Services, 2nd ed, Williams & Wilkins, Baltimore 1996. Title Page and Table of Contents.

University of Alberta Laboratory Chemical Safety Manual. Feb. 2003. Cover Page, Table of Contents, pp. 47-48.

Waye, Jerome T., "What is a gold standard for colon polyps?" *Gatroenterology* 1997;112:292-4.

Winawer et al. "Prevention of colorectal cancer: Guidelines based on new data." Bull World Health Organ 1995; 73(1):7-10.

\* cited by examiner

METHODS AND KITS FOR THE DETECTION OF ERYTHROCYTES

RELATED APPLICATIONS

This application claims the benefit of U.S. Provisional Patent Application Ser. No. 60/414,017, filed Sep. 27, 2002.

FIELD OF THE INVENTION

The invention in one embodiment provides novel methods and related kits useful in the detection of occult blood in biological samples and specimens. Such improved methods and kits can be used to screen for colorectal cancer. They can also be used to detect erythrocytes in known or suspected blood samples ex vivo, e.g., at a crime scene.

In another embodiment, the invention provides methods useful in diagnosing whether a subject is predisposed to, or suffers from, an occult-blood related disorder.

In still another embodiment, methods and kits of the invention provide a direct micro-mapping of the distribution of occluded vessels associated with cerebral vascular injury.

BACKGROUND OF THE INVENTION

Many diseases and conditions can induce internal bleeding into body fluids or excretions, but such bleeding may not always be visually detectable or apparent to a patient or healthcare provider. For example, gastrointestinal tumors and parasite infections may lead to bleeding into feces; kidney and bladder tumors may lead to bleeding into urine; lung cancer may lead to bleeding into the plural cavity; thoracic wall cancer may lead to bleeding into the thoracic cavity; and a hemorrhage may cause bleeding into the brain. This visually non-detectable bleeding is referred to as occult blood. Occult bleeding can also refer to bleeding that is clinically evident but from an obscure source.

The ability to detect occult blood is very valuable because it can allow the early diagnosis of various diseases and conditions, including but not limited to gastrointestinal tumors, kidney tumors, bladder tumors, lung cancer, thoracic wall cancer, as well as parasite infestation. Importantly, early detection, diagnosis, and treatment for many of these disease and conditions can greatly increase a patient's chance of vurvival. Therefore, any improvement in the sensitivity or ease of use of a test that can detect occult blood in body fluids or excretions, as well as any reduction in costs associated with that assay, can potentially save lives.

Heme is a natural pigment which combines with the protein globin to form hemoglobin. Heme is an iron complex of a class of red pigments called porphyrins. Porphyrin exists in high amounts in erythrocytes (red blood cells), and itself has a very strong fluorescence when irraidated with the appropriate wavelength of light. The fluorescence of porphyrin, however, may be quenched when its rings structure is covalently bonded with ferric ion. An important feature of porphyrins is their ability to be metalated and demetalated. A number of metals can be inserted into the porphyrin cavity by using various metal salts, for example Fe, Zn, Cu, and Ni. Previous methods have used acids of various strengths to remove the metal (demetalation) from porphyrin, thereby causing it to fluoresce, for example in the HemoQuant® and Hemoccult® II tests.

The American Gastroenterological Association (AGA) proposes that occult bleeding is the initial presentation of a positive fecal occult blood test (FOBT) result and/or iron-deficiency anemia (IDA), when there is no evidence of visible blood loss to the patient or physician. Occult bleeding can result in chronic gastrointestinal (GI) blood loss, and is usually identified only by tests that detect fecal blood or, if bleeding is sufficient, when it manifests as iron deficiency. The AGA proposes that obscure bleeding is bleeding of unknown origin that persists or recurs (i.e., recurrent or persistent IDA, FOBT positivity, or visible bleeding) after a negative initial or primary endoscopy (colonoscopy and/or upper endoscopy) result. There are two clinical forms of obscure bleeding: 1) obscure-occult identified by recurrent IDA and/or recurrent positive FOBT, and 2) obscure-overt identified by recurrent passage of visible blood.

While the focus of fecal occult blood testing is the detection of colorectal cancer, there are many causes of occult GI bleeding. Any lesion can bleed into the GI tract leading to occult GI bleeding, including but not limited to epistaxis, bleeding gums, esophagitis, peptic ulcers, esophageal and gastric malignancies, hemobilia, angiodysplasia and other benign vascular malformations such as Osler-Weber-Rendu telangiectasias, benign colon polyps, inflammatory bowel disease, ischemic bowel disease, hemorrhoids, and anal fissures. Important lesions in the upper digestive tract may be detected during the evaluation of patients who test positively for occult blood or who have iron deficiency anemia, although there is no consensus on optimal strategies for evaluating the upper digestive tract during evaluation for occult bleeding.

A major problem with screening for colon cancer through the detection of occult blood is a high rate of false-positive results, leading to invasive and expensive additional testing for healthy individuals. Additionally, commercially available fecal occult blood tests have relatively low sensitivity and positive predictive value for occult blood detection and colon cancer screening. Despite the limitations of currently available fecal occult blood tests, annual screening is recommended by the United States Preventive Services Task Force (United States Preventive Services Task Force. Guide to Clinical Preventive Services, 2nd ed, Williams & Wilkins, Baltimore 1996), the World Health Organization (Winawer et al., Prevention of colorectal cancer: Guidelines based on new data. Bull World Health Organ 1995; 73:7), and the American Cancer Society (Byers et al., American Cancer Society guidelines for screening and surveillance for early detection of colorectal polyps and cancer. Update 1997. CA *Cancer J Clin* 1997; 47:154). Most screening programs are based on the detection of occult blood along with endoscopic or radiographic evaluation of the colon. This approach has been associated with up to a 33 percent reduction in mortality from colorectal cancer (Mandel et al., *J Natl Cancer Inst* 1999; 91:434).

Commercially available tests for occult blood include HemeSelect®, FECA®, Hemoccult® II, Hemoccult II Sense®, and HemoQuant®. The likelihood that these tests will detect gastrointestinal blood is affected by the anatomical level of bleeding, factors relating to the patient (such as stool transit time, stool mixing, and intraluminal hemoglobin degradation), and the intrinsic features of the bleeding of the GI tract lesion (e.g. irregular bleeding) (Ahlquist et al., *Cancer* 1989; 63:1826–30). HemeSelect® and FECA® are based on the immunologic recognition of intact human hemoglobin, and are relatively simple and inexpensive tests. While these tests appear to have greater specificity for bleeding sources in the colon, bleeding from upper GI sources may not be detected because as blood passes through the GI tract the hemoglobin may be sufficiently altered so that it is not recognized immunologically. Thus, while immunological tests have a theoretical advantage in terms of localizing bleeding to the lower GI tract, the use of the tests are limited by the inability to detect blood loss originating in the upper GI tract, loss of globin antigenicity at room temperature, and the requirement for laboratory processing.

Hemoccult® II and Hemoccult II Sensa® are guaiac-based fecal occult blood tests that make use of the pseudoperoxidase activity of hemoglobin, and have been widely used and extensively evaluated. Guaiac turns blue after oxidation by oxidants or peroxidases in the presence of an oxygen donor such as hydrogen peroxide. Since heme, either as intact hemoglobin or free heme, has pseudoperoxidase activity, it can be detected through the use of guaiac. Hemoccult® II is a widely used guaiac test for fecal occult blood, and Hemoccult II Sensa® is another guaiac test that is more sensitive to peroxidase-like materials (Allison et al., *N Engl J Med* 1996; 334:155–59). When either of these tests is used, patients are instructed to diet for at least two days and up to one week prior to the test. The diet typically involves no red meat or turnip/horseradish, no gastric irritant drugs, no aspirin or other nonsteroidal anti-inflammatory drugs, no vitamin C, and an increased intake of high fiber foods. Additionally, while fecal rehydration can markedly raise the sensitivity of these tests, it can also reduce specificity (Mandel et al., *N Engl J Med* 1993; 328:1365–71).

The likelihood that a guaiac-based test will be able to detect occult bleeding is generally proportional to the quantity of fecal heme, which in turn is related to the size and location of the bleeding lesion. Thus, these types of tests are generally best at detecting large, more distal lesions. But these guaiac-based tests are also inconsistent in their accuracy. For example, one study of the Hemoccult® II test found that fecal hemoglobin levels must exceed 10 mg per gram of stool (10 ml of daily blood loss) for the test to be positive 50 percent of the time, but stools containing hemoglobin levels of less than 1 mg per gram can result in a positive test (Stroehlein et al., *Am J Dig Dis* 1976; 21:841–44; Ahlquist, Approach to the patient with occult gastrointestinal bleeding. In: Yamada T, ed. Textbook of gastroenterology. 2nd ed. Vol. 1. Philadelphia: J. B. Lippincott, 1995: 699–717; incorporated herein by reference). Such data have raised questions about the accuracy of these types of tests for detecting colonic lesions (Lang and Ransohoff, *JAMA* 1994; 271:1011–13).

HemoQuant® is a fluorometric assay that measures heme and heme-derived porphyrin. In the upper gastrointestinal tract, hemoglobin is cleaved to form heme and globin. While some intraluminal heme (generally less than 15 percent) is reabsorbed in the small intestine, a portion of the remaining heme is converted to porphyrin and iron ("intestinal converted fraction" heme). This fraction cannot be detected by guaiac-based tests, but is detectable by HemoQuant®, which measures both heme and porphyrins and is therefore a highly accurate indicator of bleeding, regardless of whether the bleeding occurs in the upper, middle, or lower GI tract. Moreover, substances that may interfere with or cause false positive results for guaiac-based tests (e.g., vegetable peroxidases) do not affect the test. Another advantage of HemoQuant® is that, unlike the guaiac and immunologic tests, it can give quantitative assessments of blood loss. The main disadvantage of this test is that it is expensive and requires a more complicated laboratory technique, and therefore cannot be performed at the bedside or in the office.

Accordingly, the need exists for a simple test for occult blood that incorporates the advantages of the heme-porphyrin test and is free of the disadvantages of known guaiac-based and fluorescence-based tests. A simple and more economical test that would reduce the likelihood of false positive and negative readings would be a significant improvement in the art and could potentially save numerous lives.

Erythrocyte detection in tissues or blood vessels can also prove to be highly significant in the detection and treatment of cerebral vascular injuries.

When the main blood supply to a particular region of brain is abruptly stopped, the pathophysiological changes are different between the central and peripheral regions of the involved area. Acute neuronal death occurs within the first hour of initial loss of blood flow in the central region (ischemic core), whereas some of the neurons in peripheral regions (ischemic penumbra) undergo slow degeneration over a period of several hours-days (Hermann et al., *Neuroscience* 104, 947–955 (2001)). In contrast to the core, the penumbra undergoes dynamic changes throughout the ischemia and reperfusion process, and it may coalesce either with the ischemic core or the normal tissue depending on the reperfusion conditions. A significant therapeutic goal of clinical management in stroke patients is to salvage the viable tissue in this penumbra.

Local pre-ischemic circulatory conditions at the capillary level may not be fully restored for an extended period of time after blood flow is resumed in the major arteries, thereby rendering the penumbra volume vulnerable to a much longer period of partial ischemia. This condition has in the past been termed the "no-reflow" phenomenon (Ames et al., *Am J Pathol.* 52, 437–453 (1968)), and describes a microvasculature perfusion failure after cerebral ischemia and reperfusion.

Partial microcirculatory stasis after cerebral ischemia and reperfusion is a potential factor in delayed cell death in occluded blood vessels. Sometimes described as the "no-reflow" phenomenon, such partial microcirculatory stasis may contribute to the developing damage in ischemic penumbra region and lead to additional injury following reperfusion. Limitations in current detection techniques have left the extent and spatial distribution of the phenomenon undetermined, and have in fact raised questions as to its existence.

Accordingly, the need exists for a test that will establish the existence of the "no-reflow" phenomenon and provide a technique to establish the extent and spatial distribution of the phenomenon in connection with the diagnosis and treatment of subjects that are prone to, or have suffered from, cerebral vascular trauma.

SUMMARY OF THE INVENTION

The invention provides novel methods and related kits useful in the detection of occult blood in biological samples and specimens such as feces, urine, cerebral spinal fluid, fluid from the plural cavity, cerebral fluid, and other body fluids or excretions. Methods and kits of the invention may be used to detect occult blood in any animal with blood, in particular vertebrates and mammal, preferably humans. Importantly, methods of the invention improve the sensitivity for detecting occult blood.

In another embodiment, the invention provides methods useful in diagnosing whether a subject is predisposed to, or suffers from, an occult-blood related disorder.

In still another embodiment, methods of the invention provide a direct micro-mapping of the distribution of occluded vessels associated with cerebral vascular injury. The invention provides novel methods and related kits useful in determining the extent and spatial distribution of the "no-reflow" phenomenon in connection with the diagnosis and treatment of subjects that are prone to, or have suffered from, cerebral vascular trauma.

In another embodiment, the invention provides methods useful in determining the presence or past existence of erythrocytes in known or suspected blood samples ex vivo, e.g., at a crime scene.

The methods of the invention exploit the fluorescence of native porphyrin species contained in erythrocytes (red blood cells) to detect occult blood. A strong reducing agent is used to render erythrocytes highly fluorescent. While not wishing to be bound by any particular theory, such fluorescence is probably the result of liberating the ferric ion from its quenching position in the porphyrin ring of hemoglobin. For example, when sodium borohydride, a strong reducer, is reacted with porphyrin, porphyrin releases the ferric ion, thereby forming a porphyrin-like product with greatly enhanced fluorescence.

More specifically, in the methods of the instant invention a strong reducing agent, such as sodium borohydride, is believed to remove the ferric ion from the porphyrin structure, thereby generating a porphyrin-like product with dramatically increased fluorescence intensity. Sodium borohydride, when dissolved in aqueous solution, releases a hydrogen atom, which is a strong reducer. This hydrogen atom reacts with heme derived iron-porphyrin and causes the iron to be released. The aforementioned sequence provides one sequence of reactions that are likely to occur in methods of the invention and is no way limits the scope of the claimed methods.

Methods of the invention produce a porphyrin-like product, the fluorescence of which is greatly enhanced because the fluorescence of the porphyrin-like product is no longer quenched by iron. After a brief reaction time, for example from about 10 to about 20 minutes, the porphyrin-like product fluoresces with a characteristic spectrum, which can be accurately detected by a fluorescence spectrometer or a fluorescence microscope. Since porphyrin exists in great amounts in erythrocytes, this method can be used to accurately detect even trace amounts of blood or blood decomposition derivatives in nearly any solution or matter, including biological specimens and samples, as well as human fluids or excretions, with the sensitivity limit being a single erythrocyte.

The term "porphyrin-like product" as used herein refers to a product that results after the removal of iron from the ring structure of porphyrin; a product with an altered configuration resulting from the demetalization of porphyrin; a product with an altered configuration resulting from the removal of the ferric ion from porphyrin; a product that fluoresces with a broad spectrum from about 450 nm to about 750 nm, for example, a product that fluoresces with a broad spectrum from about 530 to about 670 nm when excited at approximately 480 nm; a product that has two broad peaks between about 500 nm to about 650 nm when excited at about 500 nm, for example a product that has two broad peaks between about 556 and about 590 nm when excited at approximately 480 nm; and/or a product that fluoresces maximally at between about 500 nm to about 650 nm, for example a product that fluoresces maximally at approximately 556 nm when excited at about 480 nm.

In a preferred embodiment, the invention provides a method for detecting occult blood in a specimen comprising: (a) treating the specimen with a reacting solution comprising a strong reducing agent, wherein the strong reducing agent reduces porphyrin to a porphyrin-like product; and (b) monitoring for the fluorescence of a porphyrin-like product in the treated specimen; wherein fluorescence of the porphyrin-like product indicates the presence of occult blood. In a preferred embodiment, the strong reducing agent is sodium borohydride. In another preferred embodiments, the reacting solution is made up of approximately 0.1 percent to approximately 4 percent sodium borohydride, and in a particularly preferred embodiment, approximately 0.2 percent sodium borohydride. In yet another preferred embodiment, the reacting solution is primarily composed of phosphate buffered saline (PBS). In a preferred embodiment, the specimen is a biological specimen, preferably feces, urine, cerebral spinal fluid, plural cavity fluid, thoracic cavity fluid, or cerebral fluid. Preferably the fluorescence of the porphyrin-like product is monitored by a fluorescent spectrometer or a fluorescent microscope. In a preferred embodiment the porphyrin-like product fluoresces with a broad spectrum from about 530 to about 670 nm when excited at about 480 nm.

In another preferred embodiment, the invention provides a method for detecting occult blood in a specimen comprising: (a) treating the specimen with a strong reducing agent effective to enhance the fluorescence of any porphyrin present in the specimen; and (b) monitoring for the fluorescence emitted by the treated specimen; wherein fluorescence of the treated specimen indicates the presence of occult blood. In yet another preferred embodiment, the invention provides a method that is used to detect one or more erythrocytes in a specimen, wherein the method comprises: (a) treating the specimen with a strong reducing agent effective to enhance the fluorescence of any erythrocyte present in the specimen; and (b) monitoring the fluorescence emitted by the treated specimen; wherein fluorescence of one or more erythrocytes in the treated specimen indicates the presence of erythrocytes. In a preferred embodiment, the specimen is body tissue or fluid. In another preferred embodiment, the erythrocytes are monitored by a fluorescent microscope.

In another preferred embodiment, the invention provides a method for determining or quantifying the amount of occult blood in a specimen comprising: (a) exposing the specimen to a reacting solution comprising a strong reducing agent, wherein the strong reducing agent reduces porphyrin to a porphyrin-like product; and (b) monitoring for the fluorescence of a porphyrin-like product in the treated specimen; wherein fluorescence of the porphyrin-like product indicates the amount of occult blood present in the specimen.

In another preferred embodiment, the invention provides a method for detecting fecal occult blood in a fecal specimen comprising: (a) purifying the fecal specimen to substantially remove all materials that will interfere with measuring the fluorescence properties of the fecal specimen; (b) treating the purified fecal specimen with a reacting solution comprising a strong reducing agent, wherein the strong reducing agent reduces porphyrin to a porphyrin-like product; and (c) monitoring for the fluorescence of a porphyrin-like product in the treated specimen; wherein fluorescence of the porphyrin-like product indicates the presence of occult blood in the fecal specimen.

In a still further embodiment, the invention provides a method for detecting occult blood in a specimen comprising: (a) treating the specimen with a reacting solution comprising a strong reducing agent, wherein the strong reducing agent reduces porphyrin to a porphyrin-like product; and (b) monitoring for the fluorescence of a porphyrin-like product in the treated specimen; wherein fluorescence of the porphyrin-like product indicates the presence of occult blood.

In still another embodiment, the invention provides a method for determining the extent and spatial distribution of no-reflow associated with cerebral vascular trauma comprising: (a) treating cerebral tissue with a reacting solution comprising a strong reducing agent, wherein the strong reducing agent reduces porphyrin to a porphyrin-like product; and (b) monitoring for the fluorescence of a porphyrin-like product in the treated specimen; wherein fluorescence of the porphyrin-like product indicates the extent and spatial distribution of erythrocytes trapped in cerebral tissue microvasculature.

In still another embodiment, the invention provides a method for determining the extent and spatial distribution of no-reflow associated with cerebral vascular trauma comprising: (a) treating cerebral vasculature with a reacting solution comprising a strong reducing agent, wherein the strong reducing agent reduces porphyrin to a porphyrin-like product; and (b) monitoring for the fluorescence of a porphyrin-like product in the treated specimen; wherein (1) fluorescence of the porphyrin-like product indicates the extent and spatial distribution of erythrocytes trapped in the vasculature, and (2) the vasculature is flushed with heparinized saline by cardiac perfusion to remove erythrocytes from functional post-ischemic brain microcirculation prior to treatment with the reacting solution.

In still another embodiment, the invention provides a method for detecting erythrocytes or the presence of erythrocytes at one time in a specimen or sample comprising: (a) treating the specimen or sample with a reacting solution comprising a strong reducing agent, wherein the strong reducing agent reduces porphyrin to a porphyrin-like product; and (b) monitoring for the fluorescence of the porphyrin-like product in the treated specimen or sample, wherein fluorescence of the porphyrin-like product indicates the presence of erythrocytes. Thus, in addition to measuring the existence of intact erythrocytes, the present invention contemplates detecting the presence of heme from disrupted erythrocytes, thus evidencing the existence of erythrocytes at one time in a specimen or sample.

In still other embodiments, the invention provides kits and diagnostic methods related to the aforementioned methods.

These and other aspects of the invention are described further in the following detailed description.

BRIEF DESCRIPTION OF THE FIGURES

FIG. 3a shows fluorescence visualization of erythrocytes in the capillary bed of the neocortex, and FIG. 3b shows fluorescence visualization of erythrocytes in the basal ganglia (FIG. 3b). The tissue was treated with $NaBH_4$ in both FIGS. 3a and 3b. In contrast, FIG. 3c shows a rat brain section treated exactly the same way as in FIGS. 3a and 3b, except that the $NaBH_4$ treatment step was omitted. As shown, the addition of the $NaBH_4$ treatment step allows for the visualization of erythrocytes through the enhanced fluorescence of a porphyrin-like product.

DETAILED DESCRIPTION OF THE INVENTION

1. Detection of Occult Blood

Figure 1:
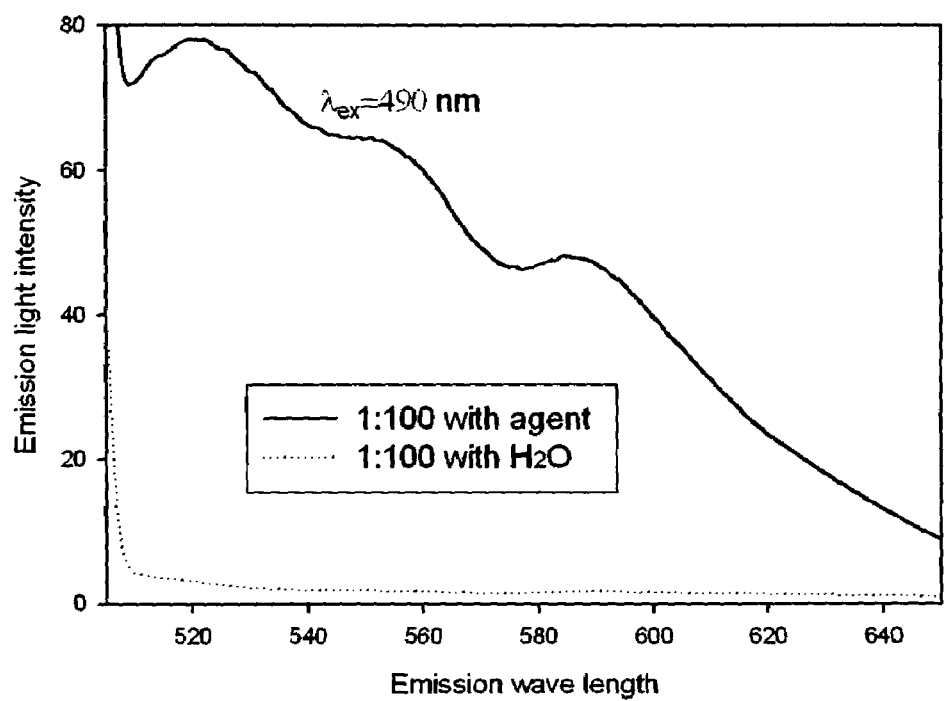
FIG. 1 illustrates fluorescence spectra of rat blood treated with borohydride and water. Rat blood was mixed with distilled water (dotted line) or borohydride (solid line) with a blood dilution ratio of 1:100. Rat blood treated with borohydride agent emitted intensive fluorescence when excited at 490 nm, while blood treated with distilled water has neglectable fluorescent emission. Note that huge difference in fluorescence intensity between the two samples.

Methods of the invention used to detect occult blood afford numerous advantages over known fecal occult blood tests such as HemoQuant®. HemoQuant® uses two reagents: oxalic acid and citric acid. In contrast, methods of the instant invention only use a single reagent. The HemoQuant® test reaction must occur at a high temperature of 110° C. for 90 minutes in the autoclave, which means the test must be done in a laboratory. In contrast, methods of the invention can be employed at room temperature. Further, sensitivity of the HemoQuant® test for colorectal cancer is only about 20–30 percent and about 13 percent for polyps (Ahlquist et al., *JAMA* 1993; 269:1262–67). Methods of the invention should prove more sensitive because the strong reducing agent employed removes ferric ion more quickly and efficiently than the acid chemistry utilized in the Hemo-Quant® test, which in turn results in a porphyrin-like product with much greater fluorescence intensity.

One of the preferred embodiments of the present disclosure is a method for detecting occult blood in a specimen comprising: (a) treating the specimen with a reacting solution comprising a strong reducing agent, wherein the strong reducing agent reduces porphyrin to a porphyrin-like product; and (b) monitoring for the fluorescence of a porphyrin-like product in the treated specimen; wherein fluorescence of the porphyrin-like product indicates the presence of occult blood. In a preferred embodiment, the strong reducing agent is sodium borohydride. In another preferred embodiment the sodium borohydride can be dissolved in an aqueous solution such as phosphate buffered saline (PBS) to make a reacting solution of 0.2 percent sodium borohydride. In other embodiments the reacting solution can be prepared as a 0.01, 0.1, 0.3, 0.4, 0.5, 0.6, 0.7, 0.8, 0.9, 1.0, 2.0, 3.0, 4.0, 5.0, 6.0, 7.0, 8.0, 9.0, or 10 percent sodium borohydride solution.

While treatment of a specimen, sample, tissue, fluid, or excretion with the reacting solution can occur at room temperature, this treatment and reaction can also occur at other temperatures, for example about 20° C., 25° C., 30° C., 37° C., 40° C., 42° C., 50° C., 55° C., 60° C., 70° C., 72° C., 80° C., 90° C., or 100° C. The reaction involving the treatment of the specimen, sample, tissue, fluid, or excretion with a reacting solution comprising a strong reducing agent is preferably substantially completed in about 5, 10, 15, 20, 25, 30, 45, or 60 minutes.

A number of strong reducing agents are available that can be used to enhance or increase the fluorescence of porphyrin or erythrocytes in accordance with the invention. The term "strong reducing agent" as used herein includes, but is not limited to, sodium borohydride, potassium borohydride, calcium borohydride, copper borohydride, ammonium borohydride, benxyltriethylammonium borohydride, benzyltriphenylphosphonium borohydride, bis(triphenylphosphine)copper(I) borohydride, cetyltrimethylammonium borohydride, lithium borohydride, methyltrioctylammonium borohydride, tetramethylammonium borohydride, tetrabutylammonium borohydride, tetraethylammonium borohydride, lithium aluminum hydride, diborane and 9-borabicyclononane (9-BBN), dihydrogen, The Grignard Reagent, dialkylcopper lithium (lithium dialkylcuprate) reagents, metallic sodium, metallo-organic alkyl sodium and metallo-organic alkyl lithium. The strong reducing agent used in the invention is preferably dissolved in an aqueous solution, preferably saline, PBS, or water (e.g., purified or distilled). Those of skill in the art will be able to identify other appropriate aqueous solutions for the strong reducing agents.

In another preferred embodiment, the invention provides a method for quantifying the amount of occult blood in a sample or specimen. One of skill in the art can use fluorescence standards to determine the amount of occult blood or erythrocytes present in a sample or specimen that is analyzed using the invention. This calculation is for an equivalent concentration of occult blood or erythrocytes because the measurement is actually the amount of porphyrin found in the sample or specimen, which can be used to determine the amount of occult blood or erythrocytes required to yield that amount of porphyrin. In one embodiment, fluorescence standards involve the use of a standard 50 μg/L solution of coproporphyrin in 1.5 mol/L HCl (Schwartz et al., *Clin Chem* 1983; 29:2061–67, incorporated herein by reference). Coproporphyrin is used as the standard reference because it is more stable than porphyrins derived from heme. Additionally, one of skill in the art can conduct experiments to detect occult blood using the invention in which a known amount of blood is added to normal feces or to a saline homogenate of feces to relate fluorescence intensity to the amount of occult blood, erythrocytes, or hemoglobin present in a sample or specimen.

Potential lesions that can lead to occult GI bleeding which may be detected by the disclosed methods may be due to mass lesions such as, for example, carcinoma (any site), large (>1.5 cm) adenoma (any site); esophageal and gastric malignancies, lymphoma, or benign colon polyps; inflammation caused by erosive esophagitis, ulcer (any site), peptic ulcer, cameron lesions, erosive gastritis, Celiac disease, Ulcerative colitis, Crohn's disease, colitis (nonspecific), inflammatory bowel disease, or idiopathic cecal ulcer; vascular disorders such as, for example, vascular ectasia (any site), portal hypertensive gastropathy or colopathy, watermelon stomach, varices (any site), hemangioma, or Dieulafoy's vascular malformation; infectious diseases caused by, for example, hookworm, whipworm, strongyloidiasis, ascariasis, tuberculous enterocolitis, or amebiasis; surreptitious bleeding such as hemoptysis or oropharyngeal bleeding (including epistaxis), and other causes such as bleeding gums, angiodysplasia and other benign vascular malformations such as Osler-Weber-Rendu telangiectasias, hemosuccus pancreaticus, hemobilia, ischemic bowel disease, carcinoid, nevus-like lesion, hemorrhoids, anal fissures, long-distance running, and factitious cause.

Methods for collecting biological samples such as feces, urine, cerebral spinal fluid, and other body fluids or excretions, which may be tested for the presence of occult blood are well known to those of skill in the art. It is well known that the predictive value of an diagnostic test may be affected in the way the test is performed or interpreted. Thus, the manner in which a positive fecal blood test was obtained are relevant factors for the interpretation of the results, and may help determine the best strategy for further investigation of the source of occult blood. Those of skill in the art understand that factors relevant to the characteristics of an occult blood test include but are not limited to the age of the patient under study, the presence of symptoms or concomitant use of medications, and family history, all of which can affect the pretest probability of disease. Other factors that affect the detection of fecal occult blood are the anatomical level of the lesion, stool transit time, stool mixing, intraluminal hemoglobin degradation, and the intrinsic features of the bleeding of a GI lesion (e.g. intermittent bleeding). Another factor is the interpretation of the results of an occult blood test. For example, in one study only 38 percent of positive stool guaiac card were correctly interpreted by program coordinators for a large multicenter trial (Fleisher et al., *Ann Intern Med* 1991; 114:875). The presently disclosed method for occult blood detection uses a fluorescence spectrometer or a fluorescence microscope to interpret the results from a sample by measuring the fluorescence of porphyrin, rather than looking for a color change in a sample, thereby reducing the likelihood of this type of interpretation error.

A patient may use a stool card to collect a stool sample, or the feces may be placed in a container such as a plastic tube with a screw on cap. These collected specimens can be stored and/or used in a fecal occult blood test. A stool card may be rehydrated before the fecal occult blood test, however this may sacrifice specificity, and therefore may not be a preferred option. A paper saddle device can also be used during the collection of stool to avoid contact with water. It is also preferable for patients to adhere to the standard dietary and medical exclusions during the week prior to sampling, although some of these restrictions will not have an effect on the method disclosed in the present disclosure (e.g., vegetable peroxidation). The handling and storage of these samples is also important to the effectiveness of fecal occult blood tests. There has been some controversy about the accuracy of fecal occult blood testing if the sample was obtained by digital rectal examination rather than spontaneous evacuation. Nevertheless, in both symptomatic and asymptomatic patients with fecal occult blood detected by digital rectal examination, the number of new lesions identified by GI evaluation is substantial (Eisner and Lewis, *Arch Intern Med* 1991; 151:2180–84). In fact, one study found a higher rate of detection of significant lesions in patients who had a positive test by digital examination than by routine screening (Rockey et al., *N Engl J Med* 1998; 339:153–59). Therefore, evaluation of these patients is important, and if symptoms are present the investigation should focus on the site or sites of the symptoms.

Preferably routine screening for fecal occult blood will include three separate stool specimens per patient. Additionally, because some neoplasms and other lesions bleed intermittently, sequential specimen samples should be tested at different times to better detect the presence of fecal occult blood. Testing can also be repeated every 6 to 12 months, particularly for those with positive fecal occult blood tests the source of which is not identified.

One preferred embodiment for detecting fecal occult blood in a fecal specimen in accordance with the instant invention comprises: (a) purifying the fecal specimen so that all materials that will interfere with measuring the fluorescence properties of the fecal specimen are removed; (b) treating the purified fecal specimen with a reacting solution comprising a strong reducing agent, wherein the strong reducing agent reduces porphyrin to a porphyrin-like product; and (c) monitoring for the fluorescence of a porphyrin-like product in the treated specimen; wherein fluorescence of the porphyrin-like product indicates the presence of occult blood in the fecal specimen. A detergent may also be included to facilitate fecal dispersion and solubilization of the porphyrin. Methods are well known to those of skill in the art for purifying fecal specimens, and are currently used for other fecal occult blood tests. One such purification method is used in the HemoQuant® test, as described in Schwartz et al., *Clin Chem* 1983; 29:2061–67, incorporated herein by reference. Preferably, a protocol will sufficiently purify a fecal specimen if it is able to remove substantially all of the materials that will interfere with measuring the fluorescence properties of the fecal specimen, for example fibers, bacteria, and chlorophylls, as well as other non-desirable materials, for example coproporphyrin and other porphyrins that are not derived from hemoglobin heme (they contain more than two carboxyl groups).

Briefly, this purification method involves a three-step solvent-extraction system for the purification of fecal porphyrins. First, the fecal specimen is well-mixed, and to the specimen is added successively 1500 µl of a 10/1 (by vol) mixture of ethyl acetate/acetic acid (EtOAc:HOAc) and 500 µl of a 3.0 mol/L solution of potassium acetate (KOAc). Vortex-mix for 15 seconds after each addition. Second, add 625 µl of the upper-phase EtOAc:HOAc extract from the first step to 250 µl of n-butanol (BuOH) and 1.9 ml of a 3 mol/L solution of KOAc in 1 mol/L KOH. Vortex-mix for 15 seconds. Third, add 250 µl of the upper-phase EtOAc:BOH extract from the second step to 750 µl of a mixture of 2 mol/L $H_3PO_4$ and HOAc (9/1, by vol), and vortex-mix for 15 seconds. The desired 2-carboxyl porphyrins are extracted in the $H_3PO_4$:HOAc (lower) phase. Those of skill in the art will also be able to improve on methods for purifying fecal specimens by routine experimentation. The removal of interfering materials by a fecal purification method is evidenced by a relatively pure emission spectrum for the porphyrin-like product.

If methods of the invention are used to test for fecal occult blood, and the test is positive, those of skill in the art will be able to perform subsequent tests based on the symptoms and condition of the patient to identify the source of the occult bleeding. The care and therapy for a patient with occult blood will be based on the abnormality identified. Whether the patient has iron-deficiency anemia is also an important clinical consideration. The GI tract of a patient can be evaluated by endoscopic evaluations (e.g. esophagogastrodudodenoscopy, enteroscopy, either of the push or Sonde type, enteroclysis, and colonoscopy) and radiographic tests (air-contrast barium enema and upper GI series). If occult bleeding is detected, the clinical focus will generally be first on colonic imaging, for example, but colonoscopy or air-contrast barium enema (Rex et al., *Gastroenterology* 1997; 112:17–23; Ferrucci, *Gastroenterology* 1997; 112:294–97; Waye, *Gastroenterology* 1997; 112:292–94; incorporated herein by reference). This imaging is used to determine if the patient has colon cancer or an adenoma. A flexible sigmoidoscopy is mandatory for patients who have the air-contrast barium enema, so the rectosigmoid colon can be fully evaluated.

An upper endoscopic examination may also be performed to determine whether the patient has a GI lesion that is bleeding located in the upper GI tract. The disclosed method for detecting occult blood may also be combined with an immunochemical test to help differentiate occult bleeding in the upper GI tract from that in the lower GI tract. Since the immunochemical test cannot detect occult bleeding in the upper GI tract, while the presently disclosed method can, a negative result for the first test and a positive result for the second test will suggest that the lesion is present in the upper GI tract. The upper GI tract should always be considered as a potential source of bleeding in a patient with normal results after a colonoscopy. In such a patient, symptoms of upper GI disorders, such as severe reflux, dyspepsia, abdominal pain, weight loss, and iron deficiency should also be assessed.

Methods of the invention may also be used to detect occult blood in a fluid sample, for example a urine sample. After the urine sample is collected, it is centrifuged and the supernatant is discarded. The pellet is resuspended in normal saline and recentrifuged. This procedure may be repeated until the pellet is sufficiently purified. The pellet is next treated with a reacting solution comprising a strong reducing agent, such as sodium borohydride, wherein the strong reducing agent reduces porphyrin present in the pellet to a porphyrin-like product. The reaction occurs in about 10 to 20 minutes, and the pellet is then washed with normal saline three times as before. In the next step the erythrocytes may be optionally lysed in 100 ml distilled water. If the presence of the erythrocytes will be visualized with a fluorescence microscope, then the erythrocytes should not be lysed. If, on the other hand, the samples are going to be analyzed with a spectrofluorimeter, the erythrocytes should be lysed and the lysates centrigured and resuspended for fluorescence analysis.

The materials and reagents required for detecting occult blood using the methods of the instant invention may be assembled together in a kit. The kits of the present invention generally will include at least the reacting solution comprising a strong reducing agent, such as sodium borohydride. In a preferred embodiment, the kit will also contain directions for gathering biological samples and specimens such as feces, urine, cerebral spinal fluid, fluid from the plural cavity, cerebral fluid, and other body fluids or excretions, and protocols for analyzing whether those samples and specimens contain occult blood, and if so, the amount of occult blood present in each positive sample. In another preferred embodiment, the kit is designed to detect fecal occult blood, and will generally include all reagents and containers necessary for collecting the fecal specimen, as well as purifying the fecal specimen so that all material that will interfere with measuring the fluorescence properties of the fecal specimen are removed.

In each case, the kits will preferably have distinct containers for each individual reagent, as well as containers for collecting and/or storing biological samples and specimens. Each reagent will generally be suitably aliquoted in their respective containers. The container means of the kits will generally include at least one vial or test tube. Flasks, bottles, and other container means into which the reagents are placed and aliquoted are also possible. The individual containers of the kit will preferably be maintained in close confinement for commercial sale. Suitable larger containers may include injection or blow-molded plastic containers into which the desired vials are retained. Instructions are preferably provided with the kit.

The material and reagents required for detecting occult blood using the methods of the invention may also be assembled into an apparatus that can be used to screen large numbers of samples and specimens simultaneously for the presence of occult blood.

Similarly, the aforementioned methods and kits are readily adaptable to detecting and examining blood samples ex vivo, e.g., at crime scenes. Methods of the invention are sufficiently robust so that they may be applied outside of a clinical or laboratory setting. In accordance with the invention, strong reducing agents may be applied to fluoresce known or suspected blood samples or stains in any variety of environments.

2. Assessing Cerebral Vascular Trauma

In a preferred embodiment, the cerebral vasculature of a subject is flushed with heparinized saline by cardiac perfusion to remove erythrocytes from the functional post-ischemic brain microcirculation. Fixed tissue is then treated with a strong reducing agent, sodium borohydride ($NaBH_4$), which renders trapped erythrocytes highly fluorescent, probably by liberating Fe from its quenching position in the porphyrin ring of hemoglobin. Application of this technique suggests not only that a significant fraction of the capillary bed is occluded but that it is blocked by trapped erythrocytes, with relatively greater trapping in the penumbra. Moreover, we have determined that the density of trapped erythrocytes shows no significant decrease following in vivo reperfusion times up to two hours. Our results show not only that oxygenation is compromised for extended periods due to the loss of flow in the capillary bed, but that erythrocytes are trapped in the vasculature for considerable periods and could therefore be a source of cytotoxic breakdown products.

Combined with perfusion fixation, methods of the invention are useful to identify non-functional capillaries following transient interruption of cerebral blood flow. We have found that: 1) Following 90 minutes of focal cerebral ischemia, the no-reflow phenomenon involved an appreciable percentage of the capillary bed and was more severe in the ischemic penumbra than in the ischemic core, and 2) In vivo reperfusion for up to 120 min did little to restore the local pre-ischemic circulatory conditions. Results from both double labeling and microcirculatory stasis index measurement showed that from 10 to 15% of the capillary volume in ischemic penumbra remained occluded after reperfusion, a very significant reduction in an active capillary bed.

The fact that an appreciable fraction of the capillary bed is functionally lost should lead to reduced oxygen and glucose levels in the territory normally served by the occluded capillaries and also to a buildup of $CO_2$ and metabolic breakdown products such as lactate. In addition, it is likely that the trapped erythrocytes, held in a deprived environment for up to 3.5 hours, will lyse due to failure of the ATP-driven Na—K pump (Mentzer et al., 1975). This would release hemoglobin, which has direct cytotoxic effects (Alayash et al., 2001), into the local environment. The above factors would be expected to produce stress on neurons and glia in the vicinity of the block, and trapped erythrocytes or microcirculatory stasis may contribute to the developing damage in penumbra.

As described in the experiments of Examples 4–7 hereinafter, we have determined that the apparent density of erythrocyte trapping assayed after 90 minutes of middle cerebral artery occlusion (MCAO) is significantly greater in the penumbra than in the core, which is consistent with the possibility of erythrocyte lysis. That is, the degree of circulatory loss is greatest in the core, and erythrocytes there might be expected to undergo a more rapid deterioration than elsewhere due to the fact that the integrity of erythrocytes is maintained by Na—K ATPase which hydrolyzes ATP as energy. The source of ATP in erythrocytes depends solely on glycolysis. Under ischemic condition, the ATP in the core will be depleted more rapidly due to dramatic reduction of blood flow, causing erythrocytes lysis to uccur, which allows a dispersion of hemoglobin leaving nothing left to fluoresce after $NaBH_4$ treatment. In the penumbra the cells would maintain their integrity for longer periods. Differences in other factors between core and penumbra could also differentially effect erythrocyte trapping in the two regions.

Based on the concept of post-ischemic erythrocyte trapping, interventions aimed merely at thrombus removal from the occluded artery to the ischemic region may not be sufficient to prevent delayed and developing injury in the penumbra, since the continued occlusion in the capillary bed may persist long after reperfusion. Therefore, therapeutic strategies to restore blood flow in the microvasculature as well as the arteries may provide substantially greater benefits.

Figure 4:
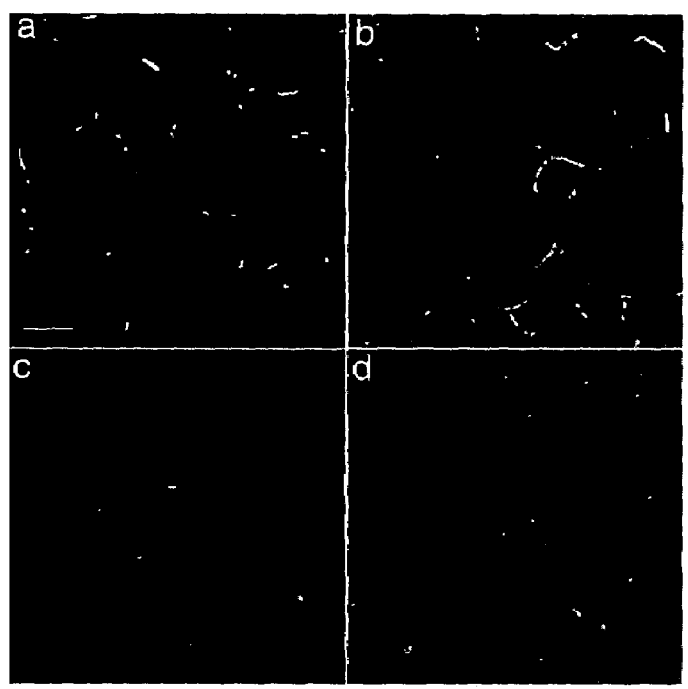
FIG. 4 illustrates autofluorescence of erythrocytes in capillaries of brain sections of ischemic rat. Differences of no-reflow phenomena between ischemic core (a) and penumbra (b) are shown in the cortex following perfusion. More erythrocytes were trapped in the capillaries of penumbra than in the ischemic core. No erythrocytes were found either in the control (no-ischemia with perfusion-fixation) rats (c), or in the contralateral hemisphere of ischemic rats (d). Scale bar, a–d, 50 μm.

One way to achieve this goal is to relieve capillary compression by virtue of reducing edema in order to open up the occluded capillaries. Another possibility is to increase oxygen supply to the no-reflow vessels. As shown in FIG. 4b, 10,000 MW of dextran can pass through erythrocyte blocked capillaries. It is likely that small oxygen-carrying molecules, such as perfluorocarbons (artificial blood), would be able to penetrate the constricted vessels, providing oxygen to the penumbra region where, if left untreated, the neurons would remain vulnerable after reperfusion. Alternatively, one could also use albumin therapy that has been shown recently to reverse stagnation, thrombosis, and corpuscular adherence within cortical venules in the reperfusion phase after focal ischemia.

$NaBH_4$ treatment, or treatment with another strong reducing agent, to enhance erythrocyte autofluorescence in conjunction with heparinized PBS perfusion in accordance with the invention is a powerful technique for visualizing capillaries that contain trapped erythrocytes. As a direct method to show microcirculation stasis, methods of the invention have a great advantage over previous approaches in that they provide a direct, micro-mapping of the distribution of occluded vessels. Previous studies using carbon suspensions or fluorescent molecules as contrast enhancers, which can infiltrate spaces not available to erythrocytes, would likely underestimate the dysfunctional, post-ischemic, capillary bed.

These and aspects of the invention are described further in the following examples, which are illustrative and in no way limiting.

EXAMPLE 1

To illustrate the improved fluorescence of samples containing red blood cells (RBCs), 100 µl samples of rat blood was collected from the tail veins of Sprague-Dawley rats (Charles River Laboratory, Wilmington, Mass., U.S.A.). The rat blood (0.1 ml) was mixed with 0.9 ml aqueous solution of our new agent, and diluted to $1:10^2$, $1:10^3$, $1:10^4$, $1:10^5$, $1:10^6$, $1:10^7$, $1:10^8$, and $1:10^9$ with phosphorus buffered solution (PBS). The mixed solutions were measured with a Shimadzu RF-1051 spectrofluorimeter. FIG. 1 shows the fluorescence spectra of rat blood treated with borohydride (solid line), and the rat blood without borohydride treatment (dashed line), both at 100 time dilution. Borohydride treated sample displayed very high fluorescence intensity, establishing the bases for detecting minute amount of blood using fluorescence technique. On the other hand, the blood sample treated only with water showed a total lack of fluorescence, suggesting that blood sample, or any chemical and biochemical existing in plasma, will not interfere with the detection of fluorescence resulting from borohydride treated blood. It is hypothesized that this increase is fluorescence is due to the reducing agent $NaBH_4$ liberating Fe from the porphyrin ring of hemoglobin, thereby no longer quenching the porphyrin fluorescence.

In FIG. 1, the spectrum of the treated blood displayed three broad peaks at 520, 555 and 590 nm, at neutral pH. These are blue-shifted from the spectral peaks of a purified porphyrin, octaethylporphyrin (Gouterman, (1978) Ch. 1. In: *The porphyrins, vol III* (Dolphin D, ed) New York: Academic Press). Separation of the peaks in the present study is approximately the same as the value reported by Gouterman (30–35 nm). Probable causes of the blue shift are reduction of double bonds within the porphyrin ring to yield others of the many fluorescent species derivable from this molecule. The characteristic orange-red band of fluorescence is a unique property of the porphyrin family among biologic molecules (Gouterman, (1978) Ch. 1. In: *The porphyrins, vol III* (Dolphin D, ed) New York: Academic Press).

EXAMPLE 2

The use of this improved method for detecting erythrocytes may also be measured by microscope visualization. For examination of cell morphology and erythrocyte fluorescence in rat brain tissue, a group of 6 Sprague-Dawley rats (Charles River Laboratory, Wilmington, Mass., U.S.A.) weighing 310 to 330 grams were anesthetized and decapitated. The brains were removed immediately and immersed in 10% formalin in 0.1 mol/L PBS for 24 hours. The brains were then rinsed thoroughly with PBS and sectioned at 50 µm using a vibratome. The tissue sections were next treated with 0.2% (W/V) $NaBH_4$ in PBS for 20 minutes, rinsed in PBS for 5 minutes, and mounted in Gel/Mount (Biomeda, Foster City, Calif., U.S.A.) on glass sides. The tissue sections were examined on a fluorescence microscope. The fluorescence of the samples was measured using a microscope equipped with epifluorescence optics (Olympus BH2-RFCA). The tissue autofluorescence was viewed using filter sets for DAPI (360 nm excitation, 400 nm dichroic, 460 nm emission), FITC (480 nm excitation, 505 nm dichroic, 535 nm emission), and TRITC (545 nm excitation, 570 nm dichroic, 610 nm emission). Images were acquired using a digital camera (Olympus MLH 020550) controlled by Olympus MagnaFire software. Freshly prepared blood smears treated with $NaBH_4$ were also examined using the fluorescence microscope.

Figure 2:
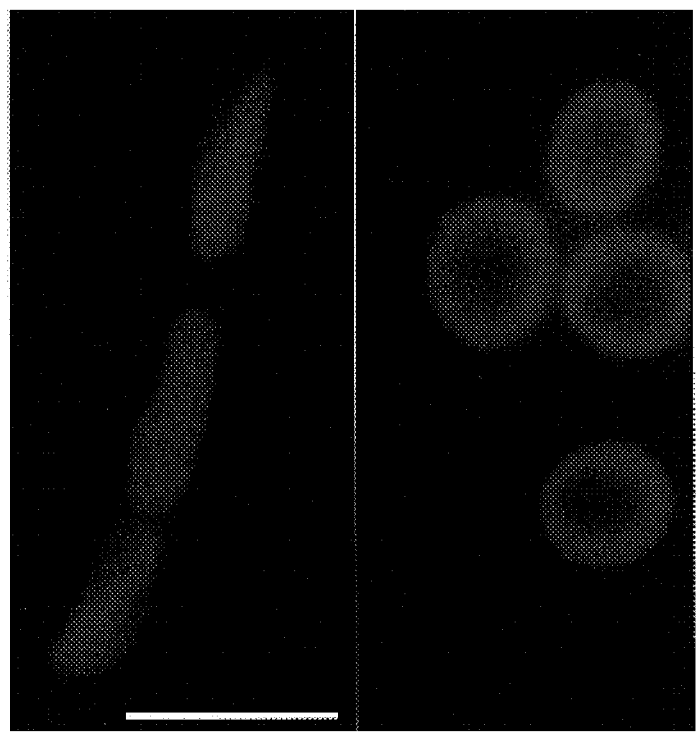
FIG. 2 illustrates typical images of the fluorescence of erythrocytes in rat brain tissue (left panel), and a rat blood smear (right panel) after being treated with a $NaBH_4$ reactive solution (Scale bar, 10 micron).

FIG. 2 shows a typical image of erythrocytes from a sample of rat brain tissue (left panel), and a typical image of erythrocytes from a rat blood smear (right panel). The fluorescence of the individual cells in the rat blood smear was diffuse and doughnut shaped with no indication of membrane localization. This visualization is consistent with the hypothesis of porphyrin fluorescence. Autofluorescence of untreated cells was less than 5% of the cells treated with $NaBH_4$.

EXAMPLE 3

This novel technique based on erythrocyte autofluorescence, which can be used to visualize the location of erythrocytes in tissue as shown in the previous example, was also used to directly visualize erythrocytes trapped in the microvascularization of brain tissue. In this experiment, a group of 6 Sprague-Dawley rats (Charles River Laboratory, Wilmington, Mass., U.S.A.) weighing 310 to 330 grams were anesthetized and decapitated. The brains were removed immediately and immersed in 10% formalin in 0.1 mol/L PBS for 24 hours. For examination of cell morphology and erythrocyte fluorescence, the brains were rinsed thoroughly with PBS and sectioned at 50 µm using a vibratome. The tissue sections were then treated with 0.2% (W/V) $NaBH_4$ (Clancy and Cauller (1998) *J Neurosci Methods* 83:97–102) in PBS for 20 minutes, rinsed in PBS for 5 minutes, and mounted in Gel/Mount (Biomeda, Foster City, Calif., U.S.A.) on glass sides. The tissue sections were then examined on a fluorescence microscope. Tissue sections were viewed using a microscope equipped with epifluorescence optics (Olympus Model BH2-RFCA). Filter set TRITC (545 nm excitation, 570 nm dichroic, 610 nm emission) was used for erythrocyte autofluorescence and cell morphology observations. Images were acquired using a digital camera (Olympus MLH 020550) controlled by Olympus MagnaFire software.

Figure 3:
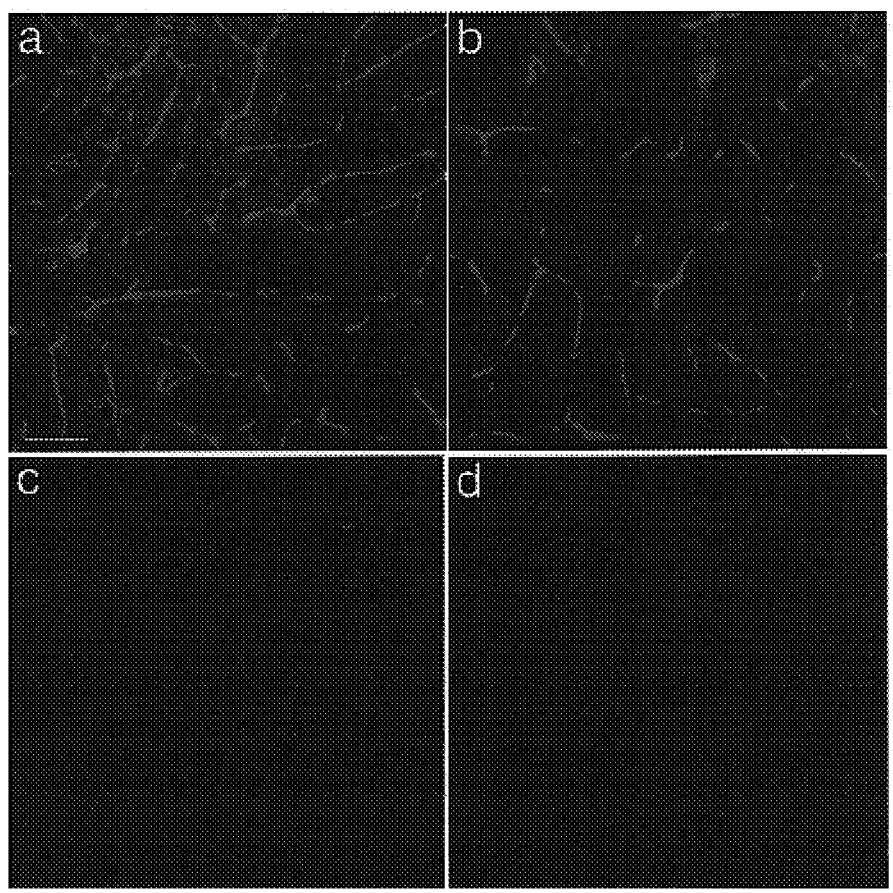
FIG. 3 illustrates fluorescence micrographs of sectioned brain tissue from rats.

FIG. 3 illustrates fluorescence visualization of the capillary bed in the neocortex (FIG. 3*a*) and basal ganglia (FIG. 3*b*) from one of the sections of rat brain fixed by immersion in 10% formalin PBS and treated with $NaBH_4$. This fixation protocol was used to gain an estimate of the total capillary bed as viewed by autofluorescence. While this pattern could be observed using either a standard fluorescein or rhodamine filter set, better contrast was obtained with the rhodamine filters. FIG. 3*c* shows a rat brain section treated exactly the same way as in FIGS. 3*a* and 3*b,* except that the $NaBH_4$ treatment step was omitted. In this section, the capillaries were indistinguishable from the background autofluorescence in both the neocortex and basal ganglia. These observations suggest that the fluorescence patterns seen in FIGS. 3*a* and 3*b* arise from erythrocytes in the brain vasculature. (See, S. Liu, J. Connor, S. Peterson, C. W. Shuttleworth, K. J. Liu, "Direct Visualization of trapped erythrocytes in rat brain following focal cerebral ischemia and reperfusion", *J. Cereb. Blood Flow Metab.*, 22, 1222–1230 (2002).

As shown in FIG. 3, the use of $NaBH_4$ treatment to enhance erythrocyte autofluorescence is a powerful technique for visualizing capillaries that contain erythrocytes.

EXAMPLE 4

To determine whether a method of the invention employing erythrocyte autofluorescence can be used to detect small amounts of blood in the upper GI tract, the protocol set forth by Rocket et al. (*Am J. Gastroenterol* 1999; 94(2):344–50, incorporated herein by reference), is utilized. One of skill in the art conducts the study using the following guidelines: Groups of 10 healthy volunteers without a history of GI disease drink 5, 10, or 20 ml of their own blood mixed with tomato juice for three to five consecutive days. Standard dietary and medication restrictions are observed. Consecutive stools are tested for two days before, as well as four days after, the ingestion of the blood. Each stool is simultaneously tested for fecal occult blood with the disclosed method (addition of the $NaBH_4$ reactive solution to the sample), as well as with the FOB tests HemoQuant®, Hemoccult II, Hemoccult II Sensa, HemeSelect, and FlexSure OBT. Fecal blood levels are recorded, and the mean fecal blood levels calculated. The proportion of positive tests for each FOB test is also compared, as well as the semiquantitative results.

EXAMPLE 5

Autofluorescence of Erythrocytes Treated with $NaBH_4$

This Example illustrates materials and methods used in the determination of the extent and spatial distribution of no-reflow associated with cerebral vascular trauma by examining cell morphology and erythrocyte fluorescence in accordance with the instant invention and as specified hereinafter in Examples 6–9.

Materials and Methods

Animals and Surgical Procedures

The Laboratory Animal Care and Use Committee of the University of New Mexico Health Science Center approved all experimental protocols.

Experimental groups: Spraque-Dawley rats (Charles River Laboratory, Wilmington, Mass.) weighing 310–330 g were randomized into the following 5 groups: Group 1, no ischemia, without perfusion fixation (see below); Group 2, no ischemia with perfusion fixation; Group 3, middle cerebral artery occlusion (MCAo) 90 minutes with perfusion fixation; Group 4, MCAo 90 minutes followed by 20 minutes of reperfusion followed by perfusion fixation; Group 5, MCAo 90 minutes followed by 120 minutes of reperfusion followed by perfusion fixation. Each group consisted of 6 rats.

Anesthesia and Perfusion Fixation

Anesthesia was induced by inhalation of 3% halothane in 70% nitrous oxide and 30% oxygen. Halothane was then reduced to 1.2% for anesthesia maintenance during the MCAo procedure. Body temperature was monitored and maintained at 37° C. Animals in Group 1 (no ischemia and without perfusion fixation) were sacrificed by decapitation while anesthetized. Brains were removed immediately and immersed in 10% formalin in 0.1 M phosphate buffer saline (PBS) for 24 hours. Animals in all other groups were sacrificed by intraaortic perfusion of 200 ml 10% formalin at a pressure of 150 cm $H_2O$ while anesthetized. Prior to the formalin perfusion, the rats were flushed thoroughly through intraaortic perfusion of heparinized PBS (12.5 U/ml). Brains were removed after formalin perfusion and immersed in 10% formalin for 24 hours of postfixation. Two additional rats in Group 5 were further perfused with 200 ml 0.017% Cascade Blue labeled dextran (Molecular Probes, D-1976)/gelatin solution after perfusion fixation.

Ischemia and Reperfusion

Middle cerebral artery ischemia and reperfusion was conducted according to the method of Longa (Longa et al., 1989) with some modifications. Briefly, a midline incision was made in the neck and the right common carotid artery (CCA), external carotid artery (ECA), internal carotid artery (ICA) and pterygopalatine artery (PPA) of ICA were exposed. The ECA was ligated. The CCA, ICA and PPA were distally closed by microclips. A loose loop was made using 4-0 silk suture around the origin of the ECA and a slit was made near the bifurcation. A silicone rubber coated monofilament nylon suture was inserted into the ICA via the ECA slit. The suture was advanced along the ICA to a distance of 18–19 mm from the bifurcation and fixed firmly at the final position by applying a microclip on the ICA. The microclips on the PPA and CCA were released and the incision was closed. The animals were allowed to recover from anesthesia during the 90 minutes of ischemia, but were re-anesthetized briefly for the reperfusion procedure. No heparin was used in the above procedures. The incision was reopened, the microclip on the ICA was removed, the blood flow was restored by gently withdrawing the suture until the suture tip reached the bifurcation and the incision reclosed. Rats were allowed to recover from anesthesia and move freely following reperfusion.

Tissue Processing

For assessment of infarction volume preliminary experiments were carried out on rats (n=20) given 90 min MCAo followed by 22.5 hours of reperfusion. Brains from these animals were sectioned at 1 mm thickness using a brain matrix. Slices were then immersed in 2% TTC (Bederson et al., 1986) in PBS for 15 min and subsequently fixed in 10% formalin in PBS.

For examination of cell morphology and erythrocyte fluorescence, brains from experimental groups (prepared as described in the anesthesia and perfusion fixation section above) were rinsed thoroughly with PBS and sectioned at 50 µm by vibratome. Sections were treated with 0.2% (W/V) $NaBH_4$ (Clancy and Cauller, 1998) in PBS for 20 min, followed by rinsing in PBS for 5 minutes, and then mounted in Gel/Mount (Biomeda, Foster City, Calif.) on glass slides to be examined on a fluorescence microscope. Cell morphorlogy from Group 4 was used to distinguish penumbra from ischemic core.

Image Acquisition and Analysis

Tissue sections were viewed using a microscope equipped with epifluorescence optics (Olympus BH2-RFCA). Filter set TRITC (545 nm excitation, 570 nm dichroic, 610 nm emission) was used for erythrocyte autofluorescence and cell morphology observation, and DAPI (360 nm excitation, 400 nm dichroic, 460 nm emission) was used for Cascade Blue observation. Images were acquired using a digital camera (Olympus MLH 020550) controlled by Olympus MagnaFire software.

Determination of Penumbra, Ischemic Core and Normal Region

It is technically difficult to distinguish the early ischemic core from the penumbra since the infarction following artery occlusion takes time to develop fully. Although there are no readily available criteria, neurons in the ischemic region with a collapsed or shrunken configuration are intensely damaged (Kalimo and Smith, *Acta Neurochir Suppl* (Wien). 36, 129–132 1986; Petito et al., 1997 *J Cereb Blood Flow Metab.* 17, 967–976; Radovsky et al., 1997 *Toxicol Pathol.* 25, 500–505). There is increasing evidence that in the early stage of ischemia the areas containing collapsed or shrunken neurons represent the developing infarction area, the ischemic core (Czurko and Nishino *Neurosci Lett.* 162, 71–74, 1993; Liu and Guo, 2000 *Neurosci Lett.* 162, 71–74; Onizuka et al., 1996 *Exp Neurol.* 137, 324–332). We considered the area containing collapsed or shrunken neurons to be early ischemic core, and the zone between the core and the normal tissue the penumbra.

Special Terms and Methods Used in Tissue Section Analysis

In order to quantify the number of capillary segments that contained trapped erythrocytes, we initially determined the no-reflow fraction. The percentage of occluded vessels, or no-reflow fraction, was defined as area of capillaries containing erythrocytes per field of view (0.58 mm$^2$) in the ischemic region divided by area of total capillaries per field of view (0.58 mm$^2$) in the corresponding regions of immersion fixed brains from control rats.

In a more comprehensive analysis, we employed an empirical parameter we termed the microcirculatory stasis index. This parameter, used as a measure of severity of the no-reflow phenomenon, was defined as the actual capillary area containing fluorescent erythrocytes in 0.58 mm$^2$. Microcirculatory stasis indices were expressed in units of $\mu m^2$ per field. Therefore, the microcirculatory stasis index for non-ischemic brain would be zero, as no erythrocytes were found in the perfusion-fixed brain sections. Six 50 $\mu m$ sections from each rat, beginning caudally from level of optic chiasma with intervals of 0.5 mm, were used for analysis. For each section, 2 images were obtained from the cortical ischemic core, 1 image from the basal ganglia ischemic core, and 2 images from cortical penumbra, all with 10× magnification. Areas of capillary fluorescence were determined using Image Pro Plus (version 4.1) software. A flattening function in the filter sets was used to minimize the effect of non-uniform excitation intensity. Segmentation thresholds were based on the intensity histogram range. Fluorescent capillaries in most images were well recognized with a threshold range of 170–196 (8 bit scale). The area of capillaries per 10× field in control rats were 4.3×10$^4$ and 4.7×10$^4$ $\mu m^2$ corresponding to ischemic core and penumbra regions in ischemic rats respectively.

Confocal Images

In addition to conventional microscopy, preparations were also examined by making a series of optical slices through 150 $\mu m$ tissue sections on a confocal microscope (Biorad MRC-600 scanning head mounted on a Zeiss IM35 microscope). Images shown in FIG. 7 were made using a 20× objective with 488 nm excitation with Z-axis steps at 5 $\mu m$.

Blood Fluorescence Spectrometry

Rat blood (100 $\mu l$) acquired from tail veins was dissolved in 1 ml normal saline. The solution was centrifuged at 2000 g for 1 minute, the supernatant was discarded and the pellet was re-suspended in 1 ml normal saline and recentrifuged. The procedure was repeated 3 times. Then the pellet was either treated with 0.2% NaBH$_4$ in normal saline or re-suspended in normal saline for 20 minutes. After washing the pellets with normal saline 3 times, erythrocytes were lysed in 100 ml of distilled water. The lysates were centrifuged at 10,000 g for 30 minutes, and the supernatants were analyzed in a 1 cm cuvette at a noise-limited low concentration in a Shimadzu RF-1501 spectrofluorimeter.

Statistics

ANOVA and Scheffe's multiple comparison was used to analyze microcirculatory stasis index, and Student's t test were used to analyze no-reflow fraction, with p<0.05 considered significant.

EXAMPLE 6

Determining Perfusion Flow in Injured and Noninjured Tissue

Following a 90 min MCAo and a reperfusion period of either 0, 20, or 120 min, brains were flushed in situ with heparinized PBS via intracardial infusion for 20 min (200 ml) and then perfusion-fixed, sliced and treated with NaBH$_4$. Without the MCAo step, the subsequent procedures produced the near blank micrographs typified by FIG. 2c. In the MCAo animals however, trapped erythrocytes were found in many of the capillaries of the ischemic core (FIG. 4a) and penumbra (FIG. 4b). On the contralateral side of the brain, which received no insult, there was no erythrocyte fluorescence (FIG. 4d), establishing that there is a marked difference in the threshold of perfusion flow for erythrocyte removal between the 2 regions. No erythrocytes were trapped in arterioles and venules of any region.

Figure 5:
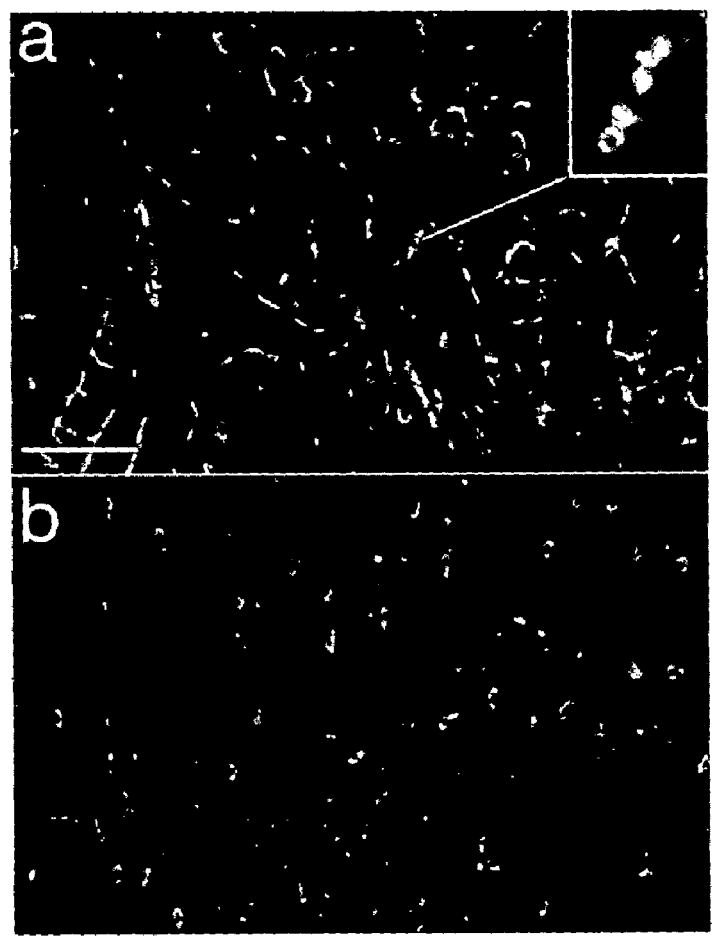
FIG. 5 illustrates image stacks acquired by confocal microscopy from brain sections of rats subjected to 90 min MCAo and 20 min of reperfusion. The images are a composite of 15 optical sections taken at 5 μm steps from 150 μm brain sections obtained from the penumbra region (a) or the contralateral hemisphere of the same rat (b) using a 20× objective. The inset in (a) shows a broadside view of some of the erythrocytes displaying the characteristic doughnut-shaped morphology. Scale bar, a–b, 100 μm

Sets of images were also taken from brain sections from 2 MCAo rats using a confocal microscope to generate an integrated view of the vasculature over a greater depth than conventional microscopy allows and to better demonstrate the morphology defined by the trapped erythrocytes. FIG. 5 shows composite images made by stacking optical slices over a depth of approximately 70 $\mu m$. The image of FIG. 5a taken at region P1 of the ischemic penumbra shows widely distributed fluorescent microvasculature, while the image of FIG. 5b, from the equivalent area on the contralateral side, shows only autofluorescence of neuron-shaped cells. The inset in FIG. 5a is a magnified view taken from 1 interior optical section and shows broadside views of some of the erythrocytes that display their characteristic doughnut-shaped morphology.

One estimate of the relative fraction of no-reflow to total vasculature was made as follows using conventional microscopy. Total vasculature was determined by summing the total fluorescent areas in slices from control animals whose brains had not been flushed and were immersion fixed, as in FIGS. 3a and b. No-reflow vasculature was determined as total fluorescent area from brains of ischemic animals where a heparinized PBS flush was given before perfusion fixation, as in FIG. 4. In a given animal, data were taken from 6 sequential slices matched in location of origin (see Methods). Using this method, the no-reflow fraction following 90 min MCAo, defined as total fluorescent area in ischemic animals divided by total fluorescent area in non-perfused control animals, was found to be 15.2±5.6% (n=18) in the penumbra and 8.67±3.6% (n=18) in the core. The difference is statistically significant (p<0.003, t-test).

Having established the no-reflow fraction, we have estimated the degree of capillary occlusion in subsequent experiments by expression the total area of erythrocyte fluorescence per unit area of tissue. We have termed this value a "microcirculatory stasis index", and have used this value to show that the no-reflow condition was not significantly ameliorated by reperfusion times of up to 2 hours. This surprising and critical finding is exemplified where the microcirculatory stasis index was determined as a function of reperfusion times, 0, 20, & 120 min after the standard 90 min focal ischemia. Since blood flow rapidly decreases at the onset of the focal occlusion, some of the erythrocytes trapped after 2 hours of reperfusion may actually have been in place for nearly 3.5 hours.

EXAMPLE 7

Double Imaging of Open and Occluded Vessels in Penumbra of Ischemic Rats

Figure 6:
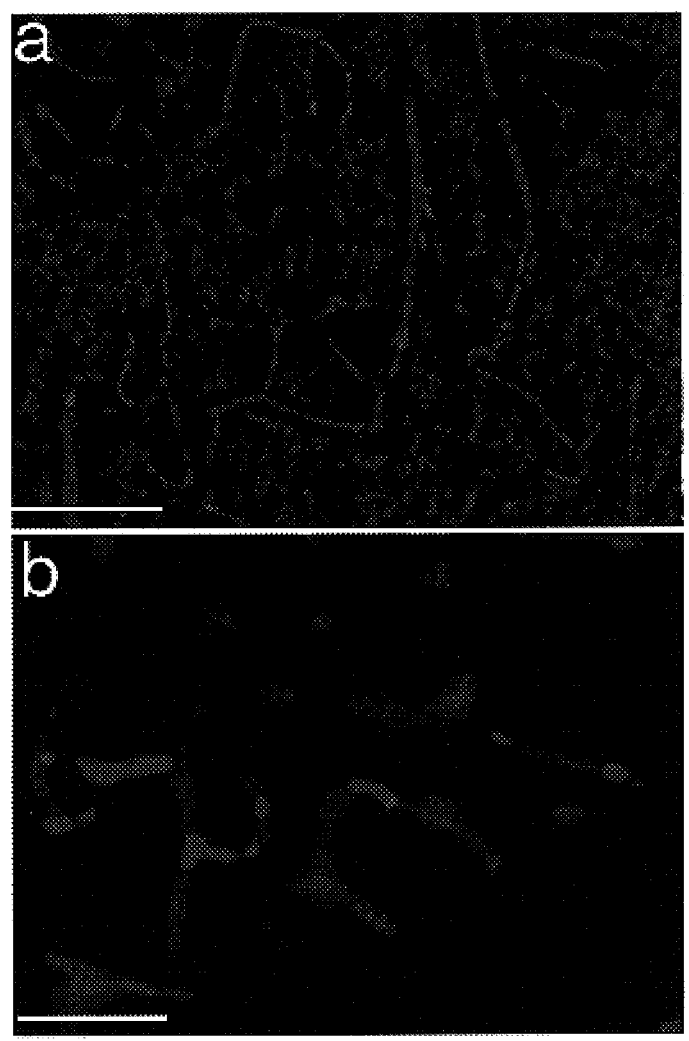
FIG. 6 illustrates visualization, in the same slice, of trapped erythrocytes and the remainder of the capillary bed. Cascade Blue dextran was used in the perfusion solution to image the capillary bed, together with autofluorescence of erythrocytes. Images were emerged digitally. a) Isolated capillaries with trapped erythrocytes (red) were demonstrated against the background of dextran perfused capillaries (blue). b) The dextran was found to pass through erythrocyte occluded capillaries and fill the capillary space between erythrocytes. Scale bar, a, 150 μm; b, 50 μm.

The determination of the fraction of occluded vessels given above has the shortcomings that different populations of rats must be used. Because this number is important in ultimately assessing how important the no-reflow condition might be in producing damage, a second approach was used. Cascade Blue-dextran (MW=10,000, 0.017%/gelatin) was perfused following perfusion fixation, under the assumption that it would not leak out of the capillary bed rapidly and would not be internalized by erythrocytes. FIG. 6a shows overlaid, true color fluorescence images of the Cascade Blue together with trapped erythrocytes thus showing open vessels and trapped erythrocytes in the same slice under identical fixation conditions. Based on these double imaging studies in 2 animals, the percentage of occluded capillaries is estimated by 10–15% of the capillary bed.

While clearly showing the extent of open capillaries, and giving reasonable agreement with our other measure of no-reflow fraction, the method as used here suffers the shortcoming that the labeled dextran appears to infiltrate capillary areas between immobile erythrocytes, as demonstrated in FIG. 6b. This leads to an underestimate of the actual amount of capillary bed lost to normal circulation since the length of vessels between trapped erythrocytes, while accessible to dextran, is functionally useless. On the other hand the experiments demonstrate directly that the occluded capillaries are still accessible to large molecules.

EXAMPLE 10

Detection Limit Comparison Between Invention and Hemoccult

An experiment was conducted to determine the detection limit for fluorescence methods of the instant invention; sensitivity of methods of the invention were compared with the currently clinically used method Hemoccult®.

Figure 7:
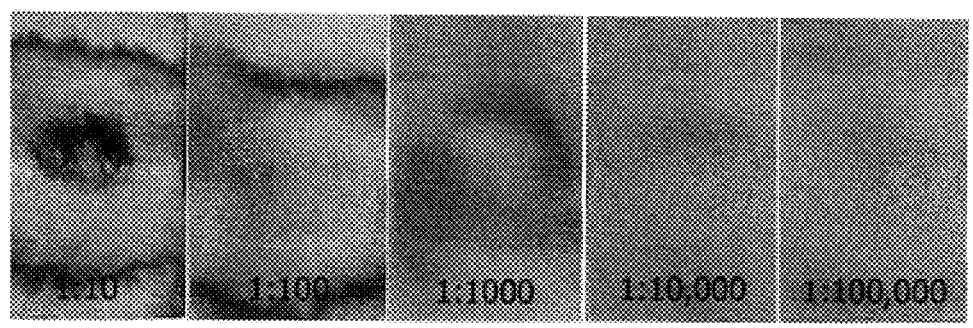
FIG. 7 illustrates the detection limit comparison between the invention and Hemoccult®. This figure illustratesx the determination of detection limit of Hemoccult® with rat blood diluted to different power. As seen in the picture above, a definite positive result is obtained with $10^3$ time dilution, while a positive result could be suspected at $10^4$ time dilution.

In the experiment, 0.2 ml rat blood was drawn from tail veins of Sprague-Dawley rats in accordance with the protocol described in Example 1. Half of the blood (0.1 ml) was mixed with 0.9 ml distilled water. The mixture was then diluted with distilled water at a factor $1:10^2$, $1:10^3$, $1:10^4$, $1:10^5$, $1:10^6$, $1:10^7$, $1:10^8$, and $1:10^9$. According to the instructions for Hemoccult®, the diluted solutions were applied to the test kit, and results are shown in FIG. 7. As can be seen, a definite positive result was obtained with $10^3$ time dilution and a suspected positive result with $10^4$ time dilution.

EXAMPLE 9

Figure 8:
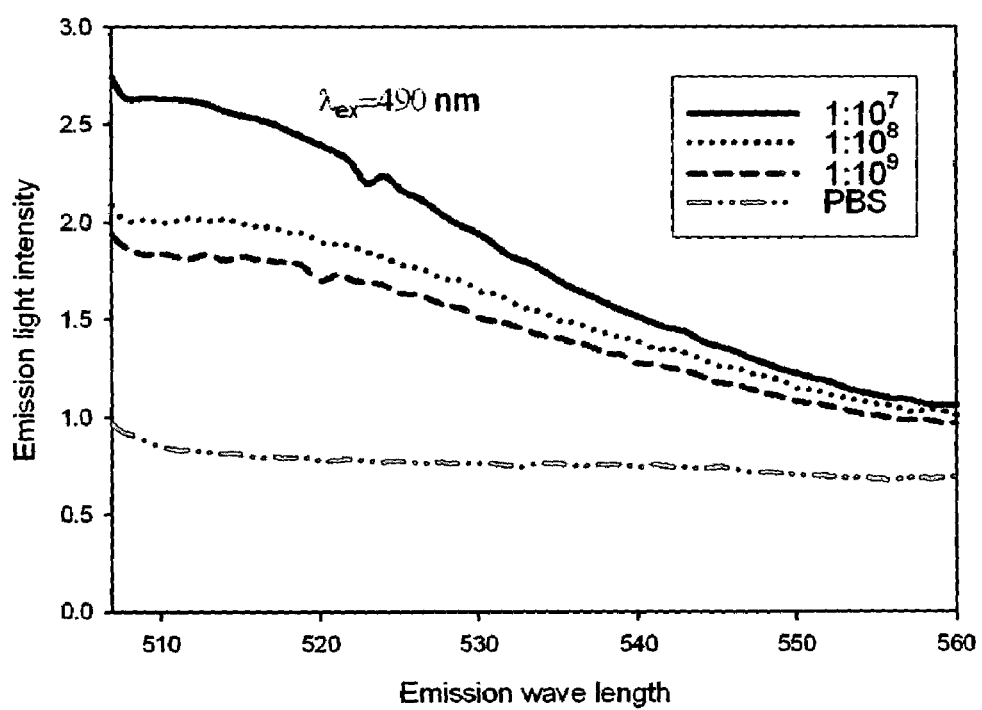
FIG. 8 illustrates the minimum concentration of blood detectable by fluorescence methods of the instant invention. This figures illustrates the determination of detection limit for the fluorescence emission from borohydride treated rat blood sample. The treated sample was diluted with phosphorus buffered solution (PBS) consecutively to $1:10^7$, $1:10^8$, $1:10^9$, and then the fluorescence intensity was measured. As seen here, a positive result can still be easily obtained when rat blood diluted even to 10 million times ($10^7$).

In order to determine the minimum concentration of blood that could be detected by fluorescence methods of the instant invention, borohydride treated blood samples described in Example 1 were diluted consecutively to a concentration of $1:10^9$. FIG. 8 shows that at dilution of $10^7$ times, we can still easily detect the fluorescence, as well as obtain the emission spectrum. In fact, even at dilution of $10^8$ or $10^9$, a detectable fluorescence could still be obtained. FIG. 8 also shows the background spectrum of pure PBS solution, which indicates zero fluorescence emission. If we use $10^7$ dilution as a comfortable limit for the convenient and accurate detection of fluorescence, and compared with the suspectible detection limit of $10^4$ for Hemoccult®, methods of the instant invention are about 1,000 time more sensitive than the current clinical standard, Hemoccult®.

It is to be understood by those skilled in the art that the foregoing descriptions and examples are illustrative of practicing the present invention, but are in no way limiting. Variations of the details presented herein may be made without departing from the spirit and scope of the present invention as defined by the following claims.

What is claimed is:

1. A method for detecting occult blood in a specimen comprising:
    (a) treating the specimen with a reacting solution comprising a strong reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(I) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
    (b) monitoring the treated specimen for fluorescence, wherein fluorescence indicates the presence of occult blood.

2. A method of claim 1, wherein the reacting solution is comprised primarily of phosphate buffered saline (PBS).

3. A method of claim 1, wherein the specimen is a biological specimen selected from the group consisting of feces, urine, cerebral spinal fluid, plural cavity fluid, thoracic cavity fluid and cerebral fluid.

4. A method of claim 1, wherein the fluorescence is monitored by a fluorescent spectrometer or a fluorescent microscope.

5. A method of claim 1, wherein the strong reducing agent is sodium borohydride.

6. A method of claim 1 wherein the specimen is a fecal specimen, the method further comprising, prior to step (a), purifying the fecal specimen to substantially remove all materials that will interfere with measuring the fluorescence of the fecal specimen.

7. A method of claim 1 wherein the treated specimen fluoresces with a spectrum from about 530 nm to about 670 nm when excited at about 480 nm.

8. A method for detecting occult blood in a specimen comprising:
    (a) treating the specimen with a reacting solution comprising a strong reducing agent; and
    (b) monitoring the treated specimen for fluorescence;
    wherein fluorescence indicates the presence of occult blood; and wherein the strong reducing agent is sodium borohydride.

9. A method of claim 8 wherein the reacting solution is made up of approximately 0.1 percent to approximately 4 percent sodium borohydride.

10. A method of claim 8 wherein the reacting solution is made up of approximately 0.2 percent sodium borohydride.

11. A method for detecting one or more erythrocytes in a specimen, wherein the method comprises:
(a) treating the specimen with a strong reducing agent effective to enhance the fluorescence of any erythrocyte present in the specimen, said reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(II) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
(b) monitoring the fluorescence emitted by the treated specimen, wherein fluorescence of one or more erythrocytes in the treated specimen indicates the presence of erythrocytes.

12. A method of claim 11 wherein the specimen is a biological specimen selected from the group consisting of feces, urine, cerebral spinal fluid, plural cavity fluid, thoracic cavity fluid and cerebral fluid.

13. A method of claim 11 wherein the erythrocytes are monitored by a fluorescent microscope.

14. A method for quantifying the amount of occult blood in a specimen comprising:
(a) exposing the specimen to a reacting solution comprising a strong reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(I) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
(b) monitoring the exposed specimen for fluorescence, wherein fluorescence indicates the amount of occult blood present in the specimen.

15. A method for determining whether a subject is at risk of developing, or suffers from, a disease associated with occult blood the method comprising:
(a) treating a specimen obtained from the subject with a reacting solution comprising a strong reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(I) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
(b) monitoring the treated specimen for fluorescence, wherein fluorescence indicates the presence of occult blood and the likelihood that the subject may develop or has developed the disease.

16. A method of claim 15 wherein the disease is gastrointestinal tumors, kidney tumors, bladder tumors, lung cancer, thoracic wall cancer, or parasite infestation and the subject is a human.

17. A method of claim 15 wherein the specimen is a biological specimen selected from the group consisting of feces, urine, cerebral spinal fluid, plural cavity fluid, thoracic cavity fluid and cerebral fluid.

18. A method for determining the extent and spatial distribution of erythrocytes trapped in cerebral tissues microvasculature comprising:
(a) treating cerebral tissue microvasculature with a reacting solution comprising a strong reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(I) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
(b) monitoring the treated tissue for fluorescence; wherein the fluorescence indicates the extent and spatial distribution of erythrocytes trapped in cerebral tissue microvasculature.

19. A method of claim 18, wherein the vasculature is flushed with heparinized saline by cardiac perfusion to remove erythrocytes from functional post-ischemic brain microcirculation prior to treatment with the reacting solution.

20. A method for determining whether a subject is at risk of developing, or suffers from, cerebral vascular trauma or bleeding, the method comprising:
(a) treating cerebral tissue microvasculature in situ or ex vivo with a reacting solution comprising a strong reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(I) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
(b) monitoring the treated tissue for fluorescence;

wherein the fluorescence indicates the extent and spatial distribution of erythrocytes trapped in cerebral tissue microvasculature which is indicative of the likelihood that the subject may develop or has developed cerebral vascular trauma or bleeding.

21. A method of detecting the presence or past existence of erythrocytes in a specimen or sample comprising:
(a) treating the specimen or sample with a reacting solution comprising a strong reducing agent selected from the group consisting of sodium borohydride, potassium borohydride, calcium borohydride, copper borohydride, ammonium borohydride, benxyltriethylammonium borohydride, benzyl-triphenylphosphonium borohydride, bis (triphenylphosphine)copper(I) borohydride, cetyl-trimethylammonium borohydride, lithium borohydride, methytrioctylammonium borohydride, tetramethylammonium borohydride, tetrabutylammonium borohydride, tetraethylammonium borohydride, lithium aluminum hydride, diborane, 9-borabicyclononane (9-BBN), dihydrogen, a grignard reagent, dialkylcopper lithium (lithium dialkylcuprate) reagents, metallic sodium, metallo-organic alkyl sodium and metallo-organic alkyl lithium; and
(b) monitoring the treated specimen or sample for fluorescence, wherein fluorescence indicates the presence or past existence of erythrocytes in the sample or specimen.

* * * * *

UNITED STATES PATENT AND TRADEMARK OFFICE
CERTIFICATE OF CORRECTION

PATENT NO. : 7,223,604 B1  
APPLICATION NO. : 10/673538  
DATED : May 29, 2007  
INVENTOR(S) : Liu et al.

It is certified that error appears in the above-identified patent and that said Letters Patent is hereby corrected as shown below:

On face page, OTHER PUBLICATIONS, after Bederson et al., please delete "Evaluation of 2, 3, 5-Triphenyltetrazolium Chloride as a Stain for Detection and Quantification of Experimental Cerebral Infraction in Rats" and replace with --"Evaluation of 2, 3, 5-Triphenyltetrazolium Chloride as a Stain for Detection and Quantification of Experimental Cerebral Infarction in Rats"--

On face page, OTHER PUBLICATIONS, after Czurko et al., please delete "'Collapsed' (argyophilic, dark) neurons in rat model of transient focal cerebral ischemia" and replace with --"'Collapsed' (argyrophilic, dark) neurons in rat model of transient focal cerebral ischemia"--

On face page, OTHER PUBLICATIONS, after Hermann et al., please delete "Relationship between metabolic dysfunctions, gene responses and delayed cell death after mild focal cerebral ischemia in mice." Neuroscience 2001;104/(4);947-955." and replace with --"Relationship between metabolic dysfunctions, gene responses and delayed cell death after mild focal cerebral ischemia in mice." Neuroscience 2001;104(4):947-955.--

In column 7, line 53, please delete "that" and replace with --the--

In claim 11, column 23, line 12, please delete "copper(ll)" and replace with --copper(l)--

Signed and Sealed this

Eleventh Day of March, 2008

JON W. DUDAS  
*Director of the United States Patent and Trademark Office*